United States Patent [19]

Phillips et al.

[11] 4,282,204

[45] Aug. 4, 1981

[54] ANTI-CARIES PREPARATIONS

[75] Inventors: Glyn O. Phillips, Clwyd, Wales; Alan N. Hall, Salford, England; Stephen D. Hogg, Liverpool, England

[73] Assignee: Nicholas Proprietary Limited, Victoria, Australia

[21] Appl. No.: 43,626

[22] Filed: May 30, 1979

[30] Foreign Application Priority Data

May 31, 1978 [GB] United Kingdom ............... 25870/78

[51] Int. Cl.³ ........................ A61K 7/16; A61K 31/70
[52] U.S. Cl. ...................................... 424/49; 424/180
[58] Field of Search .................... 424/25, 54, 180, 49, 424/361; 536/114, 48, 52

[56] References Cited

U.S. PATENT DOCUMENTS

| | | |
|---|---|---|
| 2,931,753 | 5/1960 | Chesbro et al. ........................ 424/49 |
| 3,303,184 | 2/1967 | Nordgren et al. ...................... 536/52 |
| 3,467,647 | 9/1969 | Benninga et al. ..................... 536/114 |
| 3,505,310 | 4/1970 | Nordgren et al. .................... 536/114 |
| 3,679,792 | 7/1972 | Litchfield et al. ..................... 424/48 |
| 3,928,316 | 12/1975 | Jordan et al. ......................... 536/114 |
| 4,031,307 | 6/1977 | DeMartino et al. ................. 536/114 |
| 4,053,638 | 10/1977 | Litchfield et al. ................... 424/361 |

FOREIGN PATENT DOCUMENTS 2036453 12/1970 France .

Primary Examiner—Johnnie R. Brown
Assistant Examiner—Blandel Hazel
Attorney, Agent, or Firm—Oblon, Fisher, Spivak, McClelland & Maier

[57] ABSTRACT

Cationic polysaccharides, preferably quaternary ammonium galactomannans, are used, for example in dentifrices, mouthwashes and ointments, to inhibit dental caries by binding oral bacteria.

4 Claims, 3 Drawing Figures

FIG. 2 ELUTION OF STREP. MITIS FROM DEAE CELLULOSE

ANTI-CARIES PREPARATIONS

The present invention relates to the prevention of dental caries and provides a method of inhibiting dental caries and compounds and compositions for use in said method.

Dental caries is the decay of teeth initiated by demineralization of tooth enamel by organic acids produced by bacteria e.g. Streptococcus species and Actinomyces species which ferment dietary carbohydrates and which are present in plaque deposited on the tooth surfaces. When the enamel has been penetrated, bacteria destroy the tooth protein thereby forming cavities extending into the tooth. *Streptococcus mutans* forms extracellular polysaccharides, such as dextrans and levans, which assist the bacteria in adhering to the tooth and make a substantial contribution to the plaque deposit.

Current theories of plaque formation suggest that as the tooth erupts in the mouth there is present on the enamel surface a thin organic cuticle which originates in the remains of the formative epithelium of the tooth crown. It is believed to be this cuticle which is initially colonized by plaque bacteria (see Newman, Brit. Dent. J. 1973,134,273 and 135,64 and 106). A number of workers have demonstrated the presence, intervening between the bacterial cells and the cuticle, of a material i.e. pellicle which is at least partially composed of salivary glycoproteins (see Losee et al, J. Dent. Res. 1949, 48, 512–517; Turner, Dent. Practr. Bristol, 1959, 8, 341–348; and Schule, Arch. Oral Biol. 1961, 4, 40–49). It is generally agreed that the first bacteria to be deposited on the tooth surface are streptococci and it has been suggested that certain species selectively adhere to human enamel (see van Houte et al, Arch. Oral Biol., 1970, 15, 1024–1034 and van Houte et al, Arch. Oral Biol., 1970, 16, 1131–1141). Mature plaque, for example after 24 hours, contains a greater variety of bacterial species including Actinomyces species which can constitute up to 14% of bacteria.

Traditionally, the method of preventing dental caries is to abrade plaque from the teeth by brushing with a toothbrush and, usually, an abrasive dentifrice. In recent years, fluorides have been introduced into drinking water and toothpastes to strengthen tooth enamel against decay. It has also been proposed recently to prevent dental caries by sealing occlusal surfaces with a protective polymer, to apply topical antibacterial agents and to use immunological methods. The Inventors have now found that the known methods of preventing dental caries can be at least supplemented by use of extraneous cationic (i.e. positively charged) polysaccharides to bind oral streptococci thereto.

Polysaccharides are known for use as binders, fillers and/or suspending agents in dentifrices but to the best of our knowledge all those used, or proposed to be used, in dentifrices have been anionic (i.e. negatively charged) or non-ionic. In particular, alginates; cellulose derivatives such as methylcellulose and sodium carboxymethylcellulose; dextrans; gums such as acacia (i.e. gum arabic), algaroba (i.e. locust gum), guar, karaya and tragacanth; and starches are included amongst the polysaccharides more usually employed in dentifrices.

Cationic polysaccharides are known for use as anion-exchangers and various other purposes, some of which are in the pharmaceutical art. It is relevant to this application to note that water-insoluble cationic cellulose derivatives, particularly diethylaminoethylcellulose ("DEAE-cellulose"), are known to bind certain micro-organisms and that they have been used to separate, isolate and/or purify bacteria (see Hall et al, Journal of Applied Bacteriology 1976, 41, 189–192); Trypanosoma species (see Lanham et al, Experimental Parasitology 1970, 28, 521–534); viruses (see Nicoli et al, Annales de L'Institut Pasteur 1964, 107, 192–202); and bacteriophages (see Creaser et al, Virology, 4, 200–208). It is also relevant to note that, to the best of our knowledge, water-soluble cationic polysaccharides have not been used to bind micro-organisms and it has not been proposed to use cationic polysaccharides to bind micro-organisms in vivo.

The Inventors have appreciated that, because oral cariogenic bacteria, particularly but not exclusively *Streptococcus mutans* are negatively charged, dental caries can be inhibited by binding said bacteria to an extraneous positively charged support. In particular, they have found that cationic polysaccharides are suitable for use as said supports and that water-soluble galactomannans are exceptionally useful as said supports. They believe that said use of cationic polysaccharides is a new and unobvious use for those compounds and constitutes a significant advance in the prevention of dental caries.

According to a first aspect of the present invention, there is provided a method of inhibiting dental caries which comprises contacting teeth with an extraneous pharmacologically acceptable (i.e. non-toxic) cationic polysaccharide to bind oral cariogenic bacteria to the polysaccharide. Usually, the bacteria-carrying polysaccharide will be expectorated (i.e. spat out) or rinsed from the mouth. It is much preferred that the teeth are brushed or otherwise abraded to remove plaque simultaneously with contact with the polysaccharide.

According to a second aspect of the present invention, there is provided a pharmacologically acceptable cationic polysaccharide for use in inhibiting dental caries.

According to a third aspect of the present invention, there is provided a pharmacologically acceptable cationic polysaccharide having bound thereto oral cariogenic bacteria.

According to a fourth aspect of the present invention, there is provided a composition for application to teeth, which composition comprises a pharmacologically acceptable cationic polysaccharide and a pharmacologically acceptable diluent or carrier therefor. The composition can be, for example, a dentifrice, especially a toothpaste, a mouth wash, or ointment.

According to a fifth aspect of the invention, there is provided a toothpick or gum massage stick coated or impregnated with a pharmacologically acceptable cationic polysaccharide.

The terms "pharmacologically acceptable" and "non-toxic" as used in this specification mean that the substance to which the term relates is non-toxic and has no significantly adverse effect upon the user when used in vivo in the amount and manner required to bind oral cariogenic bacteria. Further, the term "extraneous" is used herein to distinguish between naturally occurring cationic polysaccharides, if any, which might be normally present in the users mouth and cationic polysaccharides taken into the mouth for the specific purpose of inhibiting dental caries. The term "extraneous" does not preclude the use in the invention of polysaccharides identical to any such naturally occurring polysaccharides.

It is preferred that the cationic polysaccharide should have significantly greater affinity for oral bacteria than tooth enamel has for said bacteria. Suitably, the polysaccharide is a cationic derivative of a dextran, starch or cellulose although derivatives of other polysaccharides can be used. An example of a suitable cationic polysaccharide is DEAE cellulose, which is water-insoluble. It is advantageous however to use a water soluble polysaccharide to facilitate contact with the bacteria.

The cations of the polysaccharide can be primary, secondary, tertiary or quaternary amino groups; the order of preference being with increasing substitution of the amino nitrogen atom. Quaternary ammonium groups are particularly preferred.

Whilst we do not wish to be restricted to any particular theory of binding between the polysaccharide and the bacteria, we believe that the bond is usually a simple electrostatic bond and the preference for amino groups of increasing substitution is based upon this assumption. However, one class of cationic polysaccharides, viz cationic galactomannans, have been found to bind *Streptococcus mutans* to a greater extent than would have been expected from the binding power of other polysaccharides tested and which cannot be accounted for on the basis of simple electrostatic bonding or other attractive forces such as charge transfer bonds, van der Waals forces or hydrogen bonds.

The presently most preferred cationic polysaccharide is a quaternary ammonium derivative of guar gum available under the Trade Mark Jaguar C-13 for use as a flocculant in mineral processing and waste water treatment. Guar gum is a galactomannan which is present as the principal component of the endosperm of the guar plant, Cyamopsis tetragonalobus. The gum is essentially a straight chain mannan branched at regular intervals with single membered galactose units on alternate mannose units. The mannose units are linked by beta (1–4) glycoside linkages and the galactose branching is via alpha (1–6) linkages. The quaternary ammonium derivative Jaguar C13 has a degree of substitution of about 0.13 and approximates to the following formula Q represents a quaternary ammonium group The cationic polysaccharide will be used in a sufficient amount to reduce the concentration of enamel-adherent bacteria in the mouth. In the case of the preferred material Jaguar C-13, it has been found that at very low polysaccharide concentrations the concentration of adherent bacteria may actually be increased by the presence of the polysaccharide (see Experiments D hereinafter). It is believed that this effect at low concentrations is the result of interbacteria bridging. Present indications are that, at least in the case of Jaguar C-13, the cationic polysaccharide should be added in a sufficient amount to constitute at least 0.1% w/v of liquid in the mouth.

The cationic polysaccharide will usually be employed in the form of a dentifrice, especially a toothpaste. Toothpastes include an abrasive and a surfactant but those usually employed are anionic. In view of the cationic nature of the polysaccharides, the toothpaste should not contain any anionic ingredients and hence if an abrasive or surfactant is employed it should be cationic or non-ionic. An example of a suitable surfactant is an amphoteric imidazoline of the Miranol type. In the event that an anionic ingredient is employed, steps, such as coating, should be taken to ensure that it does not react with the active cationic polysaccharide content. Other ingredients which can be included in a toothpaste formulation include binders, preservatives, humectants, flavours, sweeteners and therapeutical or dental care agents. It is well within the skill of those experienced in the dentifrice art to device suitable toothpaste and other formulations for dental administration of the cationic polysaccharides.

The amount of cationic polysaccharide included in compositions of the invention will vary upon the nature of the formulation and the intended amount to be used for each treatment. As mentioned previously, there should apparently be at least 0.1% w/v of the polysaccharide in the resultant liquid content of the mouth during treatment. Thus, the compositions of the invention will usually contain at least 1% by weight of the polysaccharide, preferably at least 2%. There is no general upper limit to the concentration of polysaccharide which can be employed only any limit imposed by the chemical and/or physical requirements of the particular composition selected for use. Usually, however the amount of polysaccharide will not exceed 50% by weight.

The invention is illustrated in the following non-limiting Examples and Experiments.

EXAMPLE 1

A toothpaste in accordance with the present invention is prepared by mixing together the following ingredients:

| | % by weight |
|---|---|
| Glycerin | 15.00 |
| Saccharin Sodium | 0.20 |
| Methyl-p-hydroxybenzoate | 0.05 |
| Jaguar C-13 | 2.00 |
| Flavour | 0.80 |
| Sodium dicarboxylic cocunut imidazoline | 5.25 |
| Distilled Water | 76.70 |

The toothpaste is employed instead of conventional toothpaste to significantly decrease bacteria adhering to tooth enamel of the user.

EXAMPLE 2

Wooden gum massage sticks ("Inter-dens") of balssam or sugar pine are soaked in a 0.2% w/v aqueous Jaguar C-13 for 1 hour. The sticks are removed from the solution, placed on aluminium foil and then painted with four coats of the Jaguar C-13 solution with intermediate partial drying at 40° C. The coated sticks were completely dried at 40° C.

The treated sticks are employed instead of untreated sticks to significantly decrease bacteria adhering to tooth enamel of the user.

EXPERIMENTS A

Artificial saliva (AS)

Artificial saliva was obtained by mixing:

| | |
|---|---|
| NaCl | 0.400g |
| KCl | 0.400g |
| KH$_2$PO$_4$ | 0.430g |
| Na$_2$HPO$_4$ | 0.448g |
| Distilled water to 1 liter | |

When required, porcine mucin was dissolved in the artificial saliva at a concentration of 4 g/liter.

Cell Culture

The organisms used were strains of *Streptococcus mitis* and *sanguis*. These streptococci were maintained in Oxoid Brain Heart Infusion Broth (BHIB) in the presence of excess calcium corbonate and differentiated on Mitis-Salivarius Agar (Oxoid). Cells for adsorption studies were cultivated in BHIB (200 ml)+CaCO$_3$. The inoculum was 5 ml of a BHIB culture of the appropriate organism and growth was allowed to proceed for 18 h. at 37° C.

Preparation of cell suspensions

Cells were harvested by centrifugation at 5,000 r.p.m. for 10 min; washed three times with AS and resuspended in AS. The final suspension was made homogeneous with the aid of a laboratory mixer-emulsifier.

Estimation of cell numbers

The optical density of a test suspension of cells was measured at 600 nm and the value obtained converted to the number of cells/ml by reference to a standard curve.

Adsorption of oral streptococci by DEAE-cellulose (Whatman Advanced Ion Exchange Cellulose DE-32)

Figure 1:
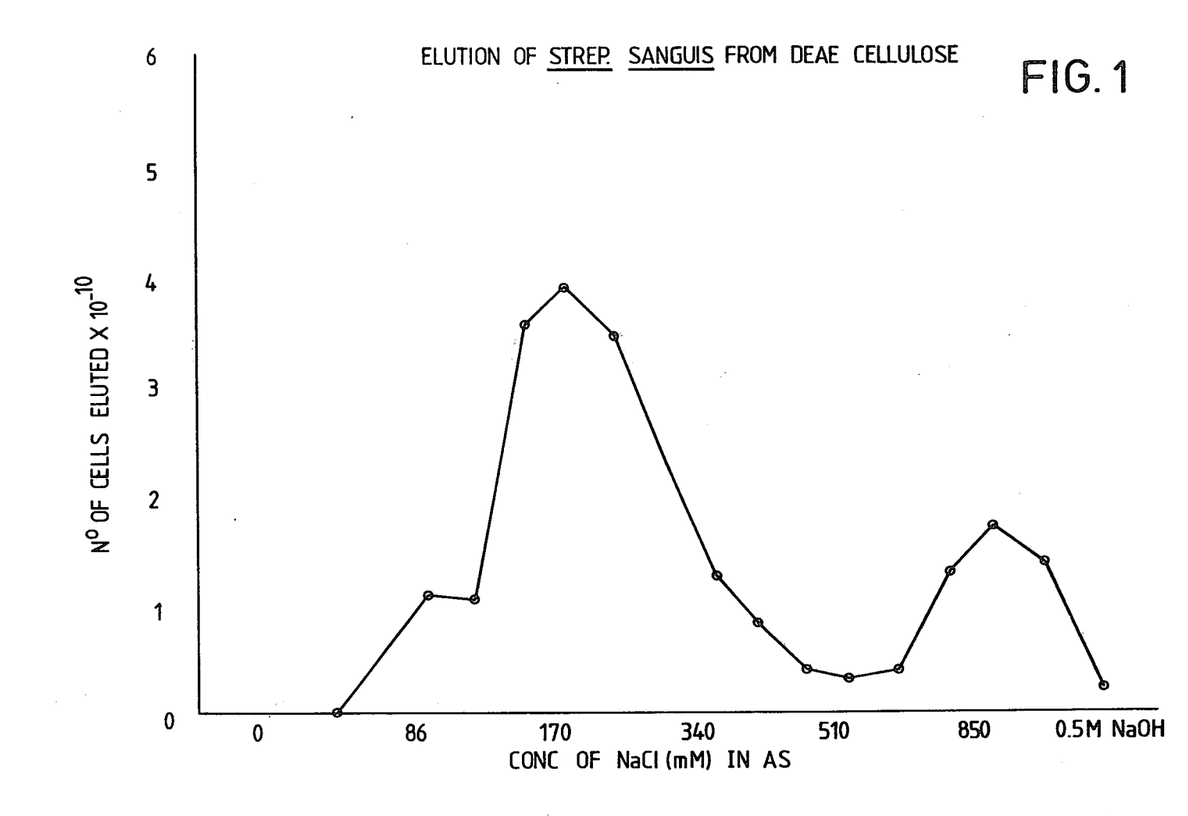
Figure 2:
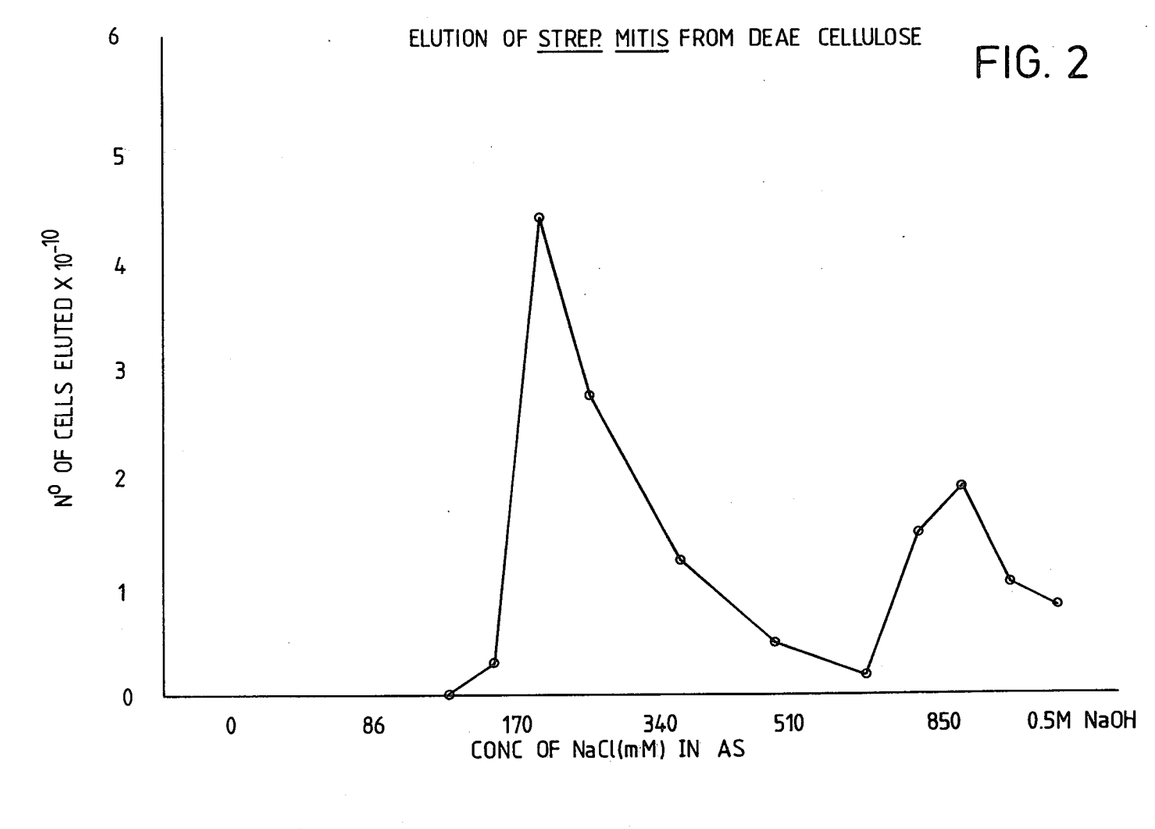

20 g. (wet weight) of DE-32, previously equilibrated with AS, was stirred with a bacterial suspension (50 ml) of known optical density for 10 min. The mixture was then filtered, under suction, through a sintered glass filter (porosity No. 4) and the optical density of the filtrate at 600 nm. recorded. Subsequently, the cellulose was resuspended in 50 ml of AS and the same sequence of operations performed. The process was repeated three times with AS and three times with each of several solutions of increasing concentrations of NaCl in AS. To complete the removal of cells the DE 32 was finally treated with 0.5 M NaOH (50 ml) and the optical density of the eluate recorded. The results are shown in FIGS. 1 and 2.

Adsorption of oral streptococci by powdered human enamel

1. Determination of the concentrations of NaCl (added to AS) which inhibit adsorption of the cells a. Coating enamel with mucin and equilibration with AS Twelve portions (50 mg) of powdered enamel (100 microns) were accurately weighed and transferred to test-tubes. Aliquots of a solution of mucin in AS(4 ml) were then added to each tube and the samples of enamel frequently stirred during a period of 30 min at room temperature. The suspensions were then centrifuged at 2,000 rpm for 10 secs and the supernatants discarded. The enamel pellets were then washed three times (by centrifugation for 10 secs) with AS to remove traces of mucin which might otherwise interfere with optical density measurements.

b. Cell suspensions in AS+NaCl

Eleven solutions of NaCl in AS, of twice the desired final concentrations of NaCl, were prepared. Aliquots of these solutions (5 ml) were then mixed with portions (5 ml) of a suspension of bacterial cells in AS; the resulting suspensions contained the required concentrations of NaCl.

c. Exposure of enamel to cells in AS+NaCl

Figure 3:
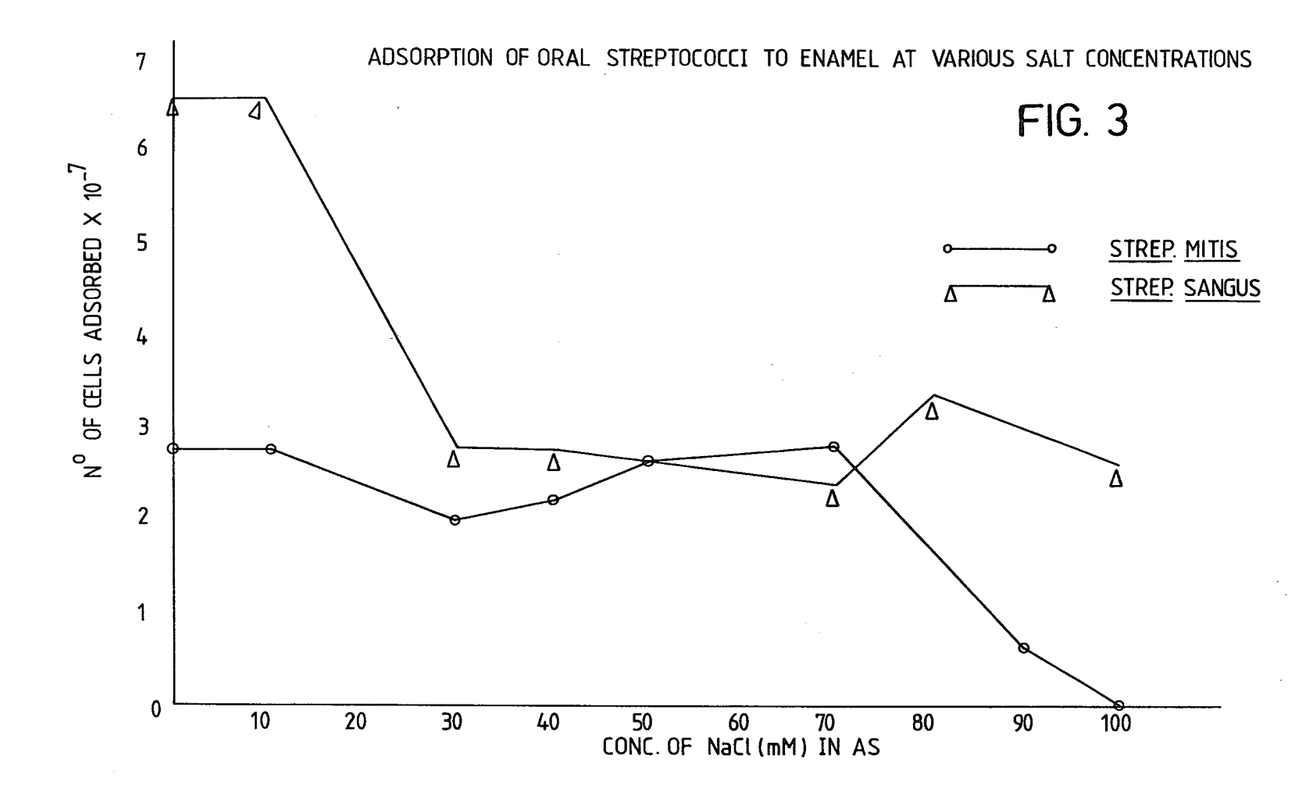

Suspensions of streptococci in AS+NaCl (4 ml) were added to each of the wet enamel samples prepared in (a). At the same time portions of the original bacterial suspension in AS were mixed with equal volumes of the AS+NaCl solutions and optical densities at 600 nm recorded. Meanwhile, the suspensions containing bacterial cells and enamel were left standing for 30 min at ambient temperature, with frequent stirring, and then allowed to settle for 5 min. A 2 ml sample of each supernatant was then taken and treated with 0.1 M EDTA (2 ml) for 15 min to remove enamel fines which would otherwise interfere with opacity measurements. The optical densities were finally read at 600 nm against a blank prepared by exposing a sample of enamel to AS for 30 min and subsequently treating the supernatant with EDTA as described. The results are given in FIG. 3.

2. Determination of the proportion of bound cells eluted from enamel by 100 mM NaCl Enamel powder (50 mg) which had been coated with mucin, equilibrated and washed with AS (as described in 1 (a)), was mixed with a bacterial suspension in AS (4 ml) of known optical density (O.D.1) and stirred intermittently for 30 min at ambient temperature. The mixture was allowed to settle for 5 min. A sample of the supernatant (2 ml) was then treated with 0.1 M EDTA (2 ml) for 15 min and optical density (O.D.2) measured against a blank prepared under the same conditions (without the addition of bacteria). The difference between O.D.1 and O.D.2 provided a measure of the number of cells bound by the enamel.

The loaded enamel was next washed three times with AS by centrifugation (2,000 r.p.m. for 10 secs) to remove any remaining unbound bacteria. The enamel pellet was then treated for 30 min with AS+100 mM NaCl (4 ml) and the optical density of the supernatant determined after removing enamel fines by addition of EDTA. The results of this experiment are given in Table I below

TABLE I

Elution of Streptococcal Cells from Powdered Enamel by 100 mM NaCl in Artificial Saliva

| | Strep. sanguis | Strep. mitis |
|---|---|---|
| Cells added to enamel (nos.) | 9.6 × 10$^8$ | 10.6 × 10$^8$ |
| Cells bound to enamel (nos.) | 2.2 × 10$^8$ | 0.8 × 10$^8$ |
| Cells eluted from enamel by 100 mM NaCl (nos.) | 1.7 × 10$^8$ | 0.65 × 10$^8$ |
| Percentage of bound cells eluted | 77% | 81% |

The results reported above show that the binding cells of two species of oral streptococci to powdered human enamel was considerably reduced by 30 mM NaCl in artificial saliva (for *Strep.sanguis*) and by 100 mM NaCl in artificial saliva (for *Strep.mitis*). Significant elution of these species from DEAE-cellulose was only observed with concentrations of NaCl >170 mM in artificial saliva. Cells of these species of streptococci appear, therefore, to be much more strongly bound to the DEAE-cellulose than to enamel powder.

EXPERIMENTS B

Materials and Methods

Buffer

Phosphate buffer (0.01 M. pH 7.0) was prepared by mixing solutions of potassium dihydrogen orthophosphate and disodium hydrogen orthophosphate.

Mucin solution

When required, porcine mucin was dissolved in buffer at a concentration of 2 g/l. The resulting suspension was clarified by centrifugation (35,000×g for 30 min).

Saliva

Stimulated saliva was collected from ten volunteers. The saliva samples were pooled, clarified by centrifugation (22,000×g for 2.5 hours) and used immediately.

DEAE-cellulose

The ion-exchange cellulose used was Whatman Advanced Ion Exchange Cellulose, Grade DE32. This cellulose derivative was pre-cycled according to the manufacturer's instructions and equilibrated with buffer. Excess buffer was removed from the DE32 by vacuum filtration which was then stored as a damp powder (DE32 slurry) in an airtight container at 4° C. The dry weight of this material was found to be 0.26 g/g of DE32 slurry.

Micro-organisms and Cultivation

The organism used was *Streptococcus mutans* NCTC 10449. It was maintained in Oxoid Brain Heart Infusion Broth (BHIB) with added sucrose (5% w/v) and on Oxoid Mitis-Salivarius Agar. Cells for experimental work were grown at 37° C. for 48 hr, without shaking, in 3×250 ml Erlenmeyer flasks each containing BHIB-sucrose (100 nl). Each flask was inoculated with a single representative colony selected from a culture of the organism on Mitis-Salivarius Agar.

Preparation of Cell Suspension

Cells were harvested by centrifugation (3000×g for 10 min), washed three times in buffer and resuspended in buffer. The final suspension was extensively homogenised with the aid of a laboratory mixer-emulsifier to shorten the long chains of cocci which are a feature of the growth of this organism. The homogenisation was continued at the highest speed setting until microscopic observation showed that the majority of cells were present as single cocci, diplococci and triplococci.

The density of cells in the final suspension was determined by measurement of the optical density of a suitable dilution and by reference to a previously prepared calibration curve.

Enamel samples

Pieces of enamel approximately 3 mm×3 mm and 1 mm in thickness were cut from the surfaces of extracted human teeth with the aid of a Dentist's drill fitted with a diamond-coated cutting disk. Care was taken to avoid eroded areas of the teeth and to ensure that, as far as possible, the enamel section chosen was flat. Three enamel pieces were fixed to each of a number of Scanning Electron Microscope (SEM) stubs with Durofix glue. In order to remove extraneous particulate matter, including bacterial cells, from the enamel surface, the tooth sections were lightly polished with an alumina powder.

SEM technique

Enamel pieces, which had been exposed to a suspension of *Strep.mutans* were fixed with the vapour from a dilute solution of formalin (5%(w/v) final concentration of HCHO) for 2 hours at room temperature. After fixation, the enamel was rinsed in three changes of distilled water and allowed to dry in air at ambient temperature. The samples were then coated with gold in an E5000 SEM Coating Unit at 1.2 Kv for 4 min in an Argon atmosphere. The final thickness of gold was 400 nm. After coating, the stubs were examined with a Cambridge Stereoscan MkIIa. (Cambridge Instruments) at a magnification of approximately 2000 times. Accurate readings of the magnification factor were made at each observation.

Each enamel piece was examined in three fields, chosen randomly, and the number of bacterial cells in each field was counted. When the number of cells present was too large to be counted accurately, a photograph of the field was prepared. The surface area of the enamel under observation was calculated from the magnification factor; the results are expressed as the total number of bacterial cells/cm$^2$.

EXPERIMENTAL DETAILS AND RESULTS

Experimental procedure

The experiments were performed in 50 ml beakers. A prepared SEM stub with attached enamel pieces was immersed in a bacterial suspension (20 ml) of known cell density. After 15 min the SEM stub was removed, rinsed gently in three changes of distilled water and fixed in formaldehyde vapour. The stubs were then coated with gold and the cell density on the surface of the enamel pieces determined by directly counting cells on the negatives of SEM photographs.

The effect of the concentration of cells in suspension on the binding of *Strep. mutans* to enamel An SEM stub, equilibrated with buffer for 24 hours, was immersed in each of a number of bacterial suspensions of varying cell density in buffer. The effect of increasing cell density in the mixture and the number of cells binding to the enamel is shown in Table II below

TABLE II

The effect of cell concentration on the binding of *Strep. mutans* to enamel

| Cell Concentration (cells . ml$^{-1}$) | Mean N° cells/field | Mean N° cells . cm$^{-2}$ Enamel |
|---|---|---|
| 1.1 × 10$^7$ | 11.3 | 0.531 × 10$^6$ |
| 1.1 × 10$^8$ | 26 | 1.31 × 10$^6$ |
| 2.2 × 10$^8$ | 54.7 | 2.64 × 10$^6$ |
| 3.3 × 10$^8$ | 79.9 | 3.84 × 10$^6$ |
| 4.4 × 10$^8$ | 106.2 | 4.95 × 10$^6$ |
| 5.5 × 10$^8$ | 2251.5 | |
| 1.1 × 10$^9$ | 2561.3 | |
| 5.5 × 10$^9$ | — | |

TABLE II-continued

The effect of cell concentration on the binding of Strep. mutans to enamel

| Cell Concentration (cells . ml$^{-1}$) | Mean N° cells/field | Mean N° cells . cm$^{-2}$ Enamel |
|---|---|---|
| 1.1 × 10$^{10}$ | — | |

The effect of Mucin on the binding of Strep.mutans to enamel

Two SEM stubs with attached enamel were equilibrated for 24 hours in buffer. The stubs were then immersed in a bacterial suspension of known cell density (3.3×10$^8$ cells.ml$^{-1}$) in buffer with added mucin (2 g/l).

The effect of DEAE-cellulose on the binding of Strep.mutans to enamel

An SEM stub with attached enamel was equilibrated in buffer for 24 hours. The stub was then immersed in a bacterial suspension of known cell density (3.3×10$^8$ cells.ml$^{-1}$) in buffer and DE32 slurry (1.0 g) added. To ensure an even distribution of DE32 the mixture was gently stirred, continuously, with a magnetic follower.

The combined effect of DEAE-cellulose and mucin on the binding of Strep.mutans to enamel The above procedure was repeated with buffer containing porcine mucine (2 g/l).

The efficacy of DE32 in the removal of Strep.mutans from enamel

The SEM stubs with attached enamel were equilibrated with buffer—and then treated with a bacterial suspension (3.3×10$^8$ cells.ml$^{-1}$) in buffer. The stubs were then rinsed with three changes of distilled water and immersed in 20 ml of buffer containing DE32 slurry (1.0 g). The mixture was stirred continuously for 15 min. before the SEM stubs were removed, rinsed in three changes of distilled water, fixed with formaldehyde vapour and examined with the SEM.

The effect of human saliva on the binding of Strep.mutans to enamel

Two SEM stubs with attached enamel were treated with clarified human saliva for 1 hour at room temperature. The stubs were then added to bacterial suspension (3.3×10$^8$ cells.ml$^{-1}$) prepared in saliva. After 15 min. the stubs were removed, and examined by means of the SEM.

The results obtained with the above treatments are given in Table III below

TABLE III

The influence of several different treatments on the binding of Strep. mutans cells to enamel

| Treatment | Mean N° cell/field | Mean N° cell . cm$^{-2}$ Enamel |
|---|---|---|
| Mucin | 32.4 | 1.59 × 10$^6$ |
| DEAE-cellulose | 17.5 | 0.831 × 10$^6$ |
| Mucin and DEAE cellulose | 6.0 | 0.3 × 10$^6$ |
| Removal of Cells by DEAE Cellulose | 39.0 | 1.925 × 10$^6$ |
| Saliva | 0 | 0 |
| None | 79.9 | 3.84 × 10$^6$ |

DISCUSSION

It can be seen from Table II that, under the experimental conditions used, there is a linear relationship between the concentration of cells in the suspending medium and the number of cells binding to a given area of the enamel. At high concentration of bacteria (greater than 5.5×10$^8$ cells.ml$^{-1}$) there was visible evidence in SEM photographs of bacterial agglutination on the enamel surface. This caused difficulty in counting the cells bound in experiments with such high concentrations of bacteria. The effect of porcine mucin, DEAE-cellulose and saliva on the density of cells binding to enamel was studied at a fixed cell density of 3.3×10$^8$ cells.ml$^{-1}$.

Table III shows that the presence of DE32 considerably reduces the number of cells binding to the enamel. At a cell concentration of 3.3×10$^8$ cells.ml$^{-1}$ the density of cells adhering to the enamel was 3.84×10$^6$ cells.cm$^{-2}$; this was reduced to 0.831×10$^6$ cells.cm$^{-2}$ in the presence of DE-32.

A reduction in the number of cells binding to the enamel was also observed when mucin (2 g/l) was incorporated in the system. (expected density, 3.84×10$^6$ cells.cm$^{-2}$; observed density, 1.59×10$^6$ cells.cm$^{-2}$). The combined effect of porcine mucin and DE32 was to reduce the number of cells binding to the enamel of 0.3×10$^6$ cells.cm$^{-2}$.

A small but appreciable reduction in the density of cells on the surface of the enamel was noted when enamel pieces with attached bacteria were treated with a suspension of DE-32. However, it is possible that this reduction may have been due to the mechanical removal of cells by agitation rather than by the DE 32.

In the presence of human saliva, no Strep.mutans cells were found to bind to the enamel. A similar result has been observed by others (Orstavik et al, Infection and Immunity (1974), 9, 794–800) and may possibly be attributed to the presence of specific bacterial agglutinins in saliva. It is however an established fact that microbial cells do adhere to the tooth surface in vivo and on the basis of the above results a reduction in the number of cells binding could be reasonably expected in the presence of DEAE-cellulose.

EXPERIMENTS C

Experiments A and B relate to an assessment of the effect of placing DEAE-cellulose in competition with human tooth enamel for cells of certain streptococci. A major disadvantage of the techniques described is that they are performed in vitro in the absence of many of the conditions unique to the human mouth. To further test the efficacy of DEAE-cellulose in the removal of oral bacteria from the mouth the following experiment was performed.

A saliva sample was taken before the teeth were brushed with either distilled water or DEAE-cellulose. Immediately after brushing and rinsing three times with distilled water a second saliva sample was taken. Dilutions of both samples were prepared in Bacteriological Ringers solution and the number of colony forming units (c.f.u.) in the original saliva samples determined by plating out a sample (0.2 ml) of a suitable dilution. Samples, in triplicate, were plated out onto both Mitis-Salivarius Agar (MSA) and Blood agar and all plates were incubated aerobically at 37° C. for 48 hours. During the counting of colonies on MSA a distinction was made between colonies of *Strep.salivarius* and other colonies.

The results given below in Table IV are a summary of the data obtained over an 8 day period. Saliva samples were taken each day immediately after brushing with either distilled water or DEAE-cellulose. The two brushing procedures were carried out on alternate days.

TABLE IV

|  | After brushing with DEAE-cellulose | After brushing without DEAE-cellulose |
| --- | --- | --- |
| % Reduction of streptococci other than *Strep. salivarius* | 86% | 73% |
| % Reduction of *Strep. salvarius* | 86% | 68% |
| % Reduction of all streptococci | 80% | 70% |
| % Reduction of total bacterial count | 51% | 41% |

These data are the means of four individual values (of three in the case of the total bacterial count). Although there is variation within each group there appears to be a definite general trend in favour of the DEAE-cellulose treatment. It should be noted that the difference between an 80% reduction in the level of streptococci in saliva and a level of 70%, in reality corresponds to a difference of 33% in the numbers of streptococci remaining.

EXPERIMENTS D

The competence of Jaguar C-13 as an inhibitor of the adhesion of bacterial cells to glass was qualitatively assessed by introducing standard glass surfaces (microscope slide coverlips) into a cell suspension in the presence and absence of selected gums under various conditions of pH value and ionic strength. For convenience and in the interests of reproducibility, the binding experiments were carried out with glass surfaces rather than dental enamel. Published work in this field recognises the use of glass as an acceptable model for binding studies (G. A. Olson, A. S. Bleiweis and P. A. Small. *Infec. Immun.* 1972, 5,(4),419–427).

CELL CULTURE

*Strep. mutans* NCTC 10449 and *Strep. sanguis* NCTC 7863 were cultured in Brain Heart Infusion broth (OXOID) with added sucrose (5% w/v). The cultures were incubated at 37° C. for 48 hours and the cells harvested by centrifugation (5000 r.p.m. for 10 mins.). The cells were washed three times and finally suspended in either Bacteriological Ringer's solution (OXOID) or distilled water. The final suspension was homogenised in a laboratory mixer-emulsifier to ensure an even distribution of cells, and diluted with either Ringer's solution or distilled water to give a final cell density of $1.0-1.5 \times 10^{-1}$ cells.ml$^{-1}$ in the test system.

PREPARATION OF GUM SOLUTION

A solution of Jaguar C-13 (0.2% or 0.4% w/v) was prepared in either Bacteriological Ringer's solution or distilled water. The solution was clarified by centriguration (5000 r.p.m. for 1 hour). Where indicated, dilutions were prepared in Bacteriological Ringer's solution.

PREPARATION OF BUFFERS

Buffer solutions were prepared (4× the final strength required) to cover a range of pH values from 2 to 13. The final concentrations of the buffer salts in the reaction mixtures were as follows.

(a) pH 1.0 to pH 4.0

Sorensen's Glycine I:—0.1 M Glycine in 0.1 M NaCl and 0.1 M HCl.

(b) pH 5.0 to pH 8.0

Sorensen's Phosphate:—0.067 M $KH_2PO_4$ and 0.067 M $K_2HPO_4$.

(c) pH 8.0 to pH 13.0

Sorensen's Glycine II:—0.1 M Glycine in 0.1 M NaCl and 0.1 M NaOH.

1. Preliminary Experiment

The extent of adhesion of streptococcal cells was assessed by immersing glass coverslips in a suspension of cells in Ringer's solution in the presence and absence of polysaccharides. After immersion for 18 hours at ambient temperature, the coverslips were gently rinsed with water and stained with methylene blue. Following further rinsing to remove excess stain, the coverslips were examined for adhering bacteria.

This limited experiment established that Jaguar C-13 (0.1% (w/v) final concentration) inhibited the binding of cells of *Strep. mutans* and *Strep. sanguis*. The inhibition of binding was found to be little affected by ionic strength, pH value or the presence of pooled clarified saliva. It was, however, profoundly affected by gum concentration. The same technique was also used to assess the performance of certain other ionic carbohydrates. It was found that the cationic polymers DEAE-cellulose (DE-23) and a cationic maize starch were also effective but less than Jaguar C-13. However, the non-ionic polymers Jaguar A-40-F and Jaguar HP-11, the anionic polymer Jaguar CMHP, an aniomic maize starch and an anionic carboxymethyl maize starch were ineffective.

The cationic maize starch had a degree of substitution 0.034–0.042 and was of the formula:

$$CH_2-O-CH_2-CHOH-CH_2N^+ (CH_3)_3 \; Cl^-$$

The anionic maize starch was a phosphate derivative having a degree of substitution of 0.04 and was of the formula:

$$CH_2-O-P\begin{matrix}O^- \\ O^-\end{matrix}$$

The carboxymethyl maize starch had a degree of substitution of 0.07–0.09 and was of the formula:

The three starches were supplied by C.P.C. (United Kingdom) Ltd.

The Jaguar polymers were all guar gums or guar gum derivatives. Jaguar A-40F is a highly purified guar gum of food grade. Jaguar HP-11 is as a hydroxypropylated guar gum having 0.35 to 0.45 moles of substitution and approximates to the formula:

JAGUAR HP-11

Jaguar CMHP is a carboxymethylated derivative of Jaguar HP-11 having a degree of substitution of about 0.06 and approximat to the formula:

JAGUAR CMHP

In order that the previously established property of Jaguar C-13 to inhibit adhesion be more fully understood an experimental method was devised to quantify its effect. This method made possible a study of the effect of gum concentration and pH value on the efficacy of Jaguar C-13 in preventing the adhesion of cells of *Strep. mutans* to glass.

2. Effect of Jaguar C-13 Concentration and Ionic Strength

Cell suspension of *Strep. mutans* NCTC 10449 in Ringer's solution (2.5 ml) and Jaguar C-13 (2.5 ml, 0.2% (w/v) and dilutions in Ringer's solution) were added to each of a number of 50 ml glass medical flats. Sodium chloride was added as required. The medical flats (lying on their wide sides) were incubated for 18 hours at room temperature. The suspensions were then gently mixed and emptied into 25 ml universal bottles. The medical flats were finally gently rinsed with Ringer's solution (5 ml) and the rinse added to the appropriate universal bottle. The number of bacterial cells in the suspension after incubation was determined by measuring the optical density at 600 nm and the number of cells binding to the surface of the glass container calculated from the change in optical density. The effect of Jaguar C-13 and sodium chloride on binding was assessed by comparing the number of cells bound in tests with controls incubated in the absence of added gum or salt. Tests with each gum dilution or salt concentration were repeated in triplicate. The results are shown in Table V below.

TABLE V

| Jaguar C-13 concentration (mg . ml$^{-1}$) | No. of *Strep. mutans* cells binding to glass (means of 3 values) ($\times 10^{-9}$) |
|---|---|
| 0 | 2.05 |
| 1.0 (i.e. .0.1% w/v) | 0 |
| 0.75 | 1.97 |
| 0.50 | 2.53 |
| 0.25 | 4.62 |
| 0.10 | 4.75 |
| 0.075 | 4.97 |
| 0.05 | 5.0 |
| 0.025 | 5.58 |
| 0.01 | 5.28 |
| 0.0075 | 4.45 |
| 0.005 | 5.23 |
| 0.0025 | 5.27 |
| 0.00025 | 3.45 |
| 0.000025 | 3.2 |
| 1.0 mg . ml$^{-1}$ + 2M NaCl | 0 |
| 0 + 2M NaCl | 2.7 |

3. Effect of pH Value a Correction for the effect of pH value on the optical density of a cell suspension Cell suspension of *Strep. mutans* NCTC 10449 (10 ml) was mixed with the appropriate buffer (10 ml). Triplicate samples (2.5 ml) were removed and each was mixed with either distilled water (2.5 ml) or Jaguar C-13 solution (2.5 ml). Distilled water (5 ml) was then added to each sample and the optical density at 600 nm recorded. The cell numbers thus determined were assumed to be the expected experimental numbers in the event of there being no cell adhesion. These data were used to calculate (by difference) the number of cells binding to the glass and should correct for experimental errors introduced by pipetting and any effect of pH value on optical density.

b Experimental method

Cell suspension of *Strep. mutans* NCTC 10449 (10 ml in distilled water) was mixed with the appropriate buffer (10 ml) and aliquots (2.5 ml), in triplicate, were removed and added to glass medical flats. Distilled water (2.5 ml) or Jaguar C-13 solution (2.5 ml, 0.2% w/v) was added as required. The suspensions were mixed and incubated at room temperature for 18 hours. The numbers of adherent cells were then determined as before, the correction factor for pH effects having been applied. The results are shown in Table VI below

TABLE VI

| pH value of medium | No. of cells ($\times 10^{-9}$) of *Strep. mutans* binding to glass (mean of 3 values) corrected for pH/OD effect | |
|---|---|---|
| | In presence of Jaguar C-13 (0.1% w/v) | In absence of Jaguar C-13 |
| 2.0 | 0.13 | 1.06 |
| 3.2 | 0 | 1.77 |
| 5.5 | 0 | 3.29 |
| 6.2 | 0.08 | 3.44 |
| 7.1 | 0.55 | 3.46 |
| 8.1 | 0.85 | 2.84 |
| 8.8 | 0.25 | 2.43 |
| 9.9 | 0.15 | 1.78 |
| 11.0 | 0.24 | 1.32 |
| 12.3 | 0.60 | 1.26 |

The results shown in Table V clearly show that Jaguar C-13, at a concentration of 1.0 mg.ml$^{-1}$ (i.e. 0.1% w/v) is very effective in preventing the adhesion of cells of *Strep. mutans* NCTC 10449 to glass. In the presence of this concentration of gum it was not possible, under the experimental conditions employed, to detect any cells binding to the glass. On the other hand, in the absence of Jaguar C-13 a mean number of $2.05 \times 10^9$ cells adhered. An interesting and reproducible feature of this experiment was the inverse dependence of adhesion on gum concentration. The number of adherent cells increased with decreasing gum concentration. At a concentration of 0.75 mg ml$^{-1}$ a mean of $1.97 \times 10^9$ cells were bound compared with $2.05 \times 10^9$ cells in the absence of the gum. As the gum concentration fell to 0.025 mg. ml$^{-1}$ the number of adherent cells increased to a maximum of $5.58 \times 10^9$. Thereafter, a fall in gum concentration resulted in a reduction in the number of adherent cells. However, at a gum concentration of 0.000025 mg.ml$^{-1}$ there was still an appreciable enhancement of binding ($3.2 \times 10^9$ bound cells).

Table VI shows that in the absence of Jaguar C-13 the number of adherent cells is, to some extent, dependent on the pH value of the environment. However, in the presence of Jaguar C-13 (1.0 mg.ml$^{-1}$) the number of cells adhering to glass was considerably reduced over the range of pH values tested (2.0 to 13.0). There was a reproducible tendency for this effect to be diminished at high pH value, i.e. above pH 9.0, but it is probable that this conclusion is exaggerated by the observed phenomenon of reduced adhesion at these pH values in the absence of gum.

In Summary, the results reported above show that the cationic carbohydrate polymers such as quaternary ammonium substituted starch, DE-23 cellulose and, in particular, Jaguar C-13 are generally effective in reducing the number of cells of *Strep. mutans* NCTC 10449 binding to glass. In contrast, anionic polymers of similar structure to those above are ineffective. In particular, in the case of Jaguar C-13 the effect is apparent at concentrations above 1.0 mg.ml$^{-1}$, over a wide pH range and at high ionic strengths.

EXPERIMENTS E

Volunteers massaged their gums by inserting wooden gum massage sticks ("Inter-dens") between their teeth at the base thereof. The message was carried out after lunch and without prior cleaning. Each volunteer first rinsed their mouth with artificial saliva and then used a treated stick of Example 2 on one half of their upper palate and an untreated stick on the other half of their upper palate. The used sticks were then placed in tubes containing 10 mls of ¾ strength Ringer's solution and left to stand for five minutes. The tubes were then vortex mixed for one minute, shaken ten times and then a loop-ful of solution was plated out on mitis-salivarins agar and incubated at 37° C. The plates were read after 72 hours for colony counts of *Streptococcus mutans* and *Streptoccus salivarius*. It was found that Jaguar coated interdens removed 225% more *Streptococcus mutans* and 128% more *Streptococcus salivarius* than the uncoated sticks.

It will be appreciated that the invention is not restricted to the particular details described above but that numerous modifications and variations can be made without departing from the scope of the invention as claimed in the following Claims.

We claim:

1. A method of inhibiting dental caries which comprises: administering to teeth a non-toxic polysaccharide selected from the group consisting of
   DEAE-cellulose, the quaternary ammonium derivative of guar gum having the repeating unit of the formula (1)

wherein Q represents a quaternary ammonium group, and cationic maize starch having a degree of substitution of 0.034–0.042 in a dental caries inhibiting amount of at least 0.1 percent w/v of mouth liquids.

2. The method according to claim 1, wherein the non-toxic cationic polysaccharide is DEAE-cellulose.

3. The method according to claim 1, wherein the non-toxic cationic polysaccharide the quaternary ammonium derivative of guar gum having the repeating unit of the formula (1).

4. The method according to claim 1, wherein the non-toxic cationic polysaccharide cationic maize starch having a degree of substitution of 0.034–0.042.

* * * * *